(12) United States Patent
Zhan et al.

(10) Patent No.: US 8,969,645 B2
(45) Date of Patent: Mar. 3, 2015

(54) PROCESS FOR REDUCING CHLORIDE IN HYDROCARBON PRODUCTS USING AN IONIC LIQUID CATALYST

(71) Applicants: Bi-Zeng Zhan, Albany, CA (US); Hye Kyung Cho Timken, Albany, CA (US); Michael Sean Driver, San Francisco, CA (US)

(72) Inventors: Bi-Zeng Zhan, Albany, CA (US); Hye Kyung Cho Timken, Albany, CA (US); Michael Sean Driver, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 252 days.

(21) Appl. No.: 13/715,873

(22) Filed: Dec. 14, 2012

(65) Prior Publication Data

US 2014/0171720 A1    Jun. 19, 2014

(51) Int. Cl.
*C07C 7/10*    (2006.01)
*B01J 31/26*    (2006.01)

(52) U.S. Cl.
CPC ... *C07C 7/10* (2013.01); *B01J 31/26* (2013.01)
USPC ........ 585/852; 208/262.1; 585/312; 585/450; 585/451

(58) Field of Classification Search
None
See application file for complete search history.

(56) References Cited

U.S. PATENT DOCUMENTS

| 3,664,966 | A |   | 5/1972 | Gordon |
|---|---|---|---|---|
| 3,981,937 | A |   | 9/1976 | Campbell et al. |
| 4,008,279 | A |   | 2/1977 | Blay |
| 5,396,002 | A | * | 3/1995 | Reed et al. ................... 570/228 |
| 6,096,680 | A |   | 8/2000 | Park |

(Continued)

FOREIGN PATENT DOCUMENTS

| EP | 0 110 377 | 1/2000 |
|---|---|---|
| EP | 0 732 316 | 1/2000 |
| WO | WO 95/05352 | 1/2000 |

OTHER PUBLICATIONS

PCT/US2013/045221, Notification of Transmittal of the International Search Report and the Written Opinion of the International Searching Authority, or the Declaration, Mailed Nov. 6, 2013, 81 Pages.

(Continued)

*Primary Examiner* — Tam M Nguyen
(74) *Attorney, Agent, or Firm* — Susan M. Abernathy

(57) ABSTRACT

We provide a process comprising:
a. feeding a chlorinated-hydrocarbon and an ionic liquid catalyst to a treatment unit;
b. operating the treatment unit at an elevated temperature to produce dechlorinated-hydrocarbon and HCl; and
c. collecting the dechlorinated-hydrocarbon, wherein at least 90 wt % of the chlorides are removed. A second process comprises:
a. creating an ionic liquid catalyst-rich zone in a distillation unit;
b. passing chlorinated-hydrocarbon to the distillation unit;
c. operating the unit under conditions causing removal of alkyl chloride to produce dechlorinated-hydrocarbon having a final boiling point close to a first final boiling point. A third process comprises:
a. feeding alkylate gasoline blending component and ionic liquid catalyst to a treatment unit;
b. operating the treatment unit; and
c. collecting a dechlorinated-hydrocarbon, wherein at least 90 wt % of the chlorides have been removed and the dechlorinated-hydrocarbon has a second RON that is close to a first RON.

26 Claims, 1 Drawing Sheet

(56) References Cited

U.S. PATENT DOCUMENTS

| | | |
|---|---|---|
| 7,538,256 B2 | 5/2009 | Driver et al. |
| 2009/0163750 A1 | 6/2009 | Timken et al. |
| 2009/0264694 A1 | 10/2009 | Driver et al. |
| 2010/0152027 A1* | 6/2010 | Lacheen et al. ............... 502/159 |
| 2012/0002475 A1 | 1/2012 | Ueno et al. |
| 2012/0165586 A1* | 6/2012 | Timken et al. ............... 585/330 |

OTHER PUBLICATIONS

U.S. Appl. No. 13/170,648, filed Jun. 28, 2011.

* cited by examiner

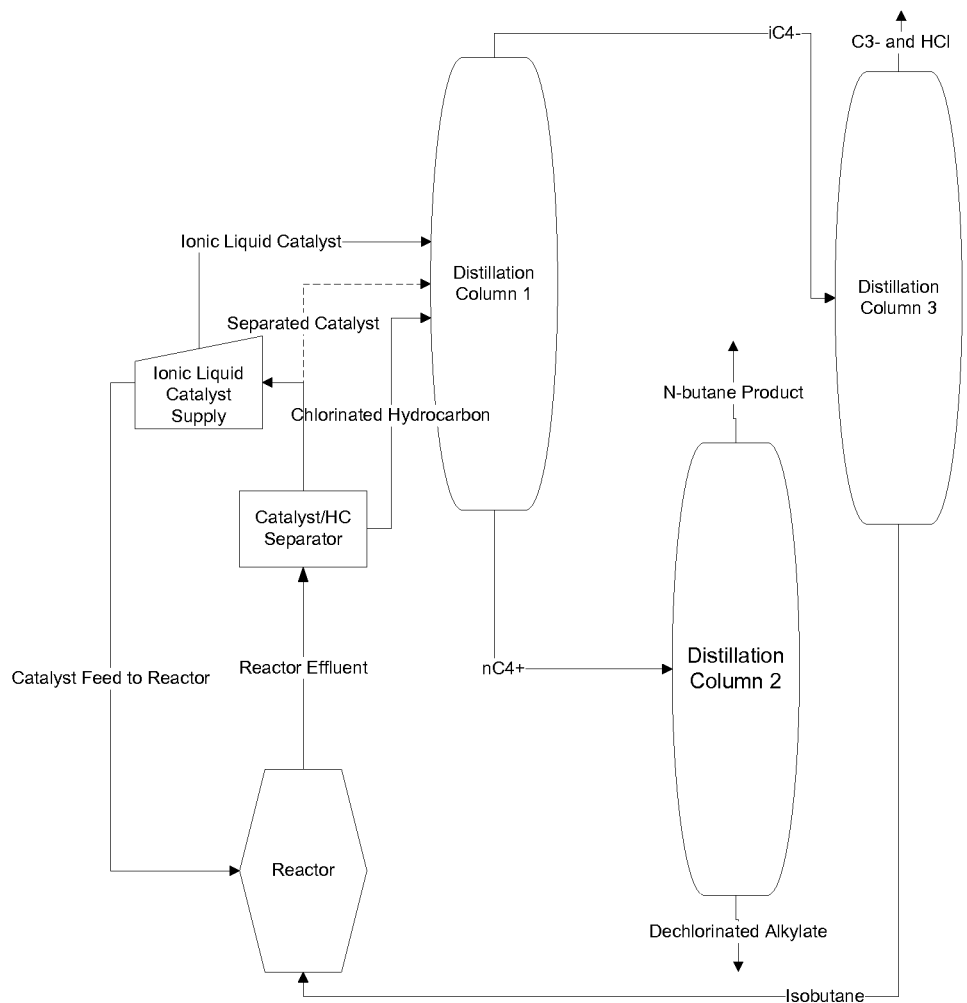

PROCESS FOR REDUCING CHLORIDE IN HYDROCARBON PRODUCTS USING AN IONIC LIQUID CATALYST

TECHNICAL FIELD

This application is directed to processes for reducing chloride in hydrocarbon products by using an ionic liquid catalyst in a treatment unit.

BACKGROUND

Earlier studies have shown that hydrocarbon conversion processes using ionic liquid catalysts comprising $AlCl_3$ produce a small amount of organic chloride impurities in the hydrocarbon products produced.

Improved processes are needed to reduce chloride in hydrocarbon products. Earlier processes have required expensive equipment, have not reduced chloride levels to an acceptably low level, have not produced both a dechlorinated-hydrocarbon and HCl, or were not known to be effective at elevated temperatures without degrading the hydrocarbon product.

SUMMARY

This application provides a process for reducing chloride in a hydrocarbon, comprising:
 a. feeding a chlorinated-hydrocarbon, comprising greater than 50 ppmw chlorides, and an ionic liquid catalyst to a treatment unit;
 b. operating the treatment unit under conditions including a temperature from 65.6° C. (150° F.) to 343° C. (650° F.), wherein the ionic liquid catalyst induces removal of an alkyl chloride in the chlorinated-hydrocarbon to produce a dechlorinated-hydrocarbon and a HCl; and
 c. collecting the dechlorinated-hydrocarbon from the treatment unit, wherein at least 90 wt % of the chlorides have been removed from the chlorinated-hydrocarbon.

This application also provides a process for producing a dechlorinated-hydrocarbon, comprising:
 a. creating an ionic liquid catalyst-rich zone in a distillation unit by feeding an ionic liquid catalyst to the distillation unit;
 b. passing a chlorinated-hydrocarbon comprising a mixture of an alkylate product and an alkyl chloride to the distillation unit;
 c. operating the distillation unit under conditions including a temperature from 65.6° C. (150° F.) to 343° C. (650° F.), wherein the ionic liquid catalyst that has accumulated in the distillation unit induces removal of the alkyl chloride to produce the dechlorinated-hydrocarbon; and wherein a second final boiling point of the dechlorinated-hydrocarbon is within 5 degrees C. of a first final boiling point of the chlorinated-hydrocarbon.

This application also provides a process for reducing chloride in a hydrocarbon, comprising:
 a. feeding a chlorinated-hydrocarbon that is an alkylate gasoline blending component comprising greater than 50 ppmw chlorides and having a first RON, and an ionic liquid catalyst to a treatment unit;
 b. operating the treatment unit under conditions including a temperature from 65.6° C. (150° F.) to 343° C. (650° F.), wherein the ionic liquid catalyst induces removal of an alkyl chloride in the chlorinated-hydrocarbon to produce a dechlorinated-hydrocarbon and a HCl; and
 c. collecting the dechlorinated-hydrocarbon from the treatment unit, wherein at least 90 wt % of the chlorides have been removed from the chlorinated-hydrocarbon and the dechlorinated-hydrocarbon has a second RON that is within 2 points of the first RON.

BRIEF DESCRIPTION OF THE DRAWINGS

FIG. 1 is a diagram of one embodiment of a process to remove chlorides from alkylate gasoline.

DETAILED DESCRIPTION

Hydrocarbons that are contaminated with chlorides can be produced by a wide range of processes. It is important to remove these chlorides to improve product properties, reduce chloride-induced corrosion, and to meet product specifications. For example, hydrocarbons that are made using catalysts comprising chloride can sometimes incorporate either trace levels or high levels of alkyl chlorides that subsequently need to be reduced. There is a concern that alkyl chlorides can create unwanted dioxins when hydrocarbons containing alkyl chlorides are combusted, such as could happen in an engine burning hydrocarbon fuel.

A chlorinated-hydrocarbon, in the context of this disclosure, has greater than 30 ppmw of chlorides, as measured by XRF Spectroscopy. In some embodiments, the chlorinated-hydrocarbon has greater than 50 ppmw, greater than 100 ppmw, greater than 250 ppmw, greater than 500 ppmw, and up to 5,000 ppmw chlorides. The chlorinated-hydrocarbon can comprise, for example, a mixture of an alkylate product, a hydrogen chloride, and an alkyl chloride. In another embodiment, the chlorinated-hydrocarbon can comprise an alkylate product or an oligomer product, and an alkyl chloride.

The chlorinated-hydrocarbon can be fed with an ionic liquid catalyst to a treatment unit. The ionic liquid catalyst can be fed together with the chlorinated-hydrocarbon to the treatment or it can be fed separately.

In the context of this disclosure, 'induces' means brings about or gives rise to.

Ionic Liquid Catalyst

Ionic liquid catalysts are very effective for catalyzing a broad range of hydrocarbon conversion reactions. Examples of hydrocarbon conversion reactions are paraffin alkylation, olefin dimerization, olefin oligomerization, concurrent alkylation and oligomerization, isomerization, aromatic alkylation, and hydrocarbon dechlorination. The ionic liquid hydrocarbon conversion reaction can be one used to make gasoline blending components, middle distillates, lubricants, or petrochemical components.

Ionic liquid catalysts are composed of at least two components which form a complex. The presence of the first component should give the ionic liquid catalyst a Lewis acidic character. The first component of the ionic liquid catalyst can comprise a Lewis Acid. The Lewis acid can be a metal halide compound selected from components such as Lewis Acidic compounds of Group 13 metals, including aluminum halides, alkyl aluminum halide, gallium halide, and alkyl gallium halide. Other Lewis Acidic compounds, such as Group 3, 4, and 5 metal halides, in addition to those of Group 13 metals, can also be used. Other specific examples include $ZrCl_4$, $HfCl_4$, $NbCl_5$, $TaCl_5$, $ScCl_3$, $YCl_3$, and mixtures thereof. In one embodiment, the ionic liquid catalyst comprises an anhydrous metal halide. Examples of anhydrous metal halides are $AlCl_3$, $AlBr_3$, $GaCl_3$, $GaBr_3$, $InCl_3$, and mixtures thereof. In one embodiment, the ionic liquid catalyst comprises an anhydrous metal chloride.

The periodic table by the International Union of Pure and Applied Chemistry (IUPAC), version date 22 Jun. 2007, is used for defining the Groups 3, 4, 5, and 13 metals. In one embodiment the first component of the ionic liquid catalyst is aluminum halide or alkyl aluminum halide. For example, aluminum trichloride can be the first component of the ionic liquid catalyst. In one embodiment the ionic liquid catalyst includes strongly Lewis acidic anions, such as $Al_2Cl_7^-$. $Al_2Cl_7^-$, for example, is a strongly Lewis acidic anion, while $AlCl_4^-$ is not. Generally, the greater the mole ratio of the first component to the second component, the greater is the acidity of the ionic liquid catalyst.

The second component making up the ionic liquid catalyst is an organic salt or mixture of salts. These salts can be characterized by the general formula Q+A−, wherein Q+ is an ammonium, phosphonium, boronium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, alkyl-aryl sulfonate, and benzene sulfonate (e.g., 3-sulfurtrioxyphenyl). In one embodiment, the ionic liquid catalyst comprises a cation that is an ammonium, phosphonium, or sulphonium. In one embodiment the second component is selected from those having quaternary ammonium halides containing one or more alkyl moieties having from about 1 to about 12 carbon atoms, such as, for example, trimethylamine hydrochloride, methyl-tributylammonium halide, or substituted heterocyclic ammonium halide compounds, such as hydrocarbyl-substituted-pyridinium halide compounds for example 1-butylpyridinium halide, benzylpyridinium halide, or hydrocarbyl-substituted-imidazolium halides, such as for example, 1-ethyl-3-methyl-imidazolium chloride.

In one embodiment the ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the ionic liquid catalyst can be an acidic haloaluminate ionic liquid catalyst, such as an alkyl substituted pyridinium chloroaluminate or an alkyl substituted imidazolium chloroaluminate of the general formulas A and B, respectively.

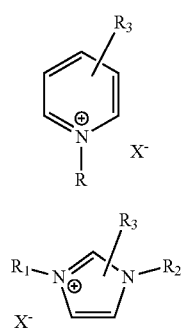

In the formulas A and B; R, $R_1$, $R_2$, and $R_3$ are H, methyl, ethyl, propyl, butyl, pentyl or hexyl group, and X is a chloroaluminate. In one embodiment the X is $AlCl_4^-$, $Al_2Cl_7^-$, or $Al_3Cl_{10}^-$. In the formulas A and B, R, $R_1$, $R_2$, and $R_3$ may or may not be the same. In one embodiment the ionic liquid catalyst is N-butylpyridinium heptachlorodialuminate $[NBuPy^+][Al_2Cl_7^-]$. In one embodiment the ionic liquid catalyst is 1-Ethyl-3-methylimidazolium heptachlorodialuminate $[emim^+][Al_2Cl_7^-]$.

In one embodiment the ionic liquid catalyst comprises a cation selected from the group of an alkyl-pyridinium, an alkyl-imidazolium, or a mixture thereof. In another embodiment the acidic ionic liquid can have the general formula RR' R" N H+ $Al_2Cl_7^-$, wherein N is a nitrogen containing group, and wherein RR' and R" are alkyl groups containing 1 to 12 carbons, and where RR' and R" may or may not be the same.

In one embodiment, the ionic liquid catalyst that is fed or passed to the treatment unit is different from a conversion-ionic liquid catalyst that was used to produce the chlorinated-hydrocarbon. In another embodiment, the ionic liquid catalyst that is fed or passed to the treatment using is the same as a conversion-ionic liquid catalyst that was used to produce the chlorinated-hydrocarbon.

Treatment Unit

The treatment unit can be any piece of equipment, or combinations of equipment, that can accommodate the ionic liquid catalyst and can be operated under conditions wherein the ionic liquid catalyst induces a removal of an alkyl chloride in the chlorinated-hydrocarbon.

Examples of treatment units that can be used include reactors and distillation units.

Examples of reactors that can be used for the treatment unit are static mixers, continuously stirred tank reactors (CSTR), nozzle reactors (including nozzle loop reactors), tubular reactors (including continuous tubular reactors), fixed bed reactors (including fixed bed contactor reactors), and loop reactors (including static mixer loop reactors). Fixed bed contactor reactors are described in US Patent Publication US 20110318233 A1.

In one embodiment, the treatment unit comprises a distillation unit and the ionic liquid catalyst has accumulated in a part of the distillation unit. In one embodiment, the treatment unit comprises a distillation column or a series of distillation columns. One embodiment of one of our processes, showing the use of a series of distillation columns as a treatment unit, is shown in FIG. 1. In another embodiment, the part of the distillation unit that has accumulated the ionic liquid catalyst is a distillation column, a bottom of a reboiler, a product-recycle loop, or combinations thereof.

In one embodiment, the ionic liquid catalyst is supported in the distillation column or the reactor used for the treatment unit. Examples of supports that can be used include porous supports, such as those comprising a refractory oxide. When used, the support can include, for example, silica, silica-alumina, alumina, zinc oxide, titania, zirconia, magnesium oxide, activated carbon, zeolites, and combinations thereof. In one embodiment the porous support is inorganic. In one embodiment the support is a polymer. The ionic liquid catalyst can be supported in the treatment unit by any type of impregnation technique, including for example: a) by soaking or with an excess of solution, b) dry or pore volume impregnation, c) incipient wetness impregnation, d) selective reaction with the surface of the support, e) percolation, f) solution co-precipitation, or g) successive impregnation. In one embodiment, the ionic liquid catalyst is supported on a polymer support by covalent bond interaction between the ionic liquid catalyst and the polymer support. These different types of impregnation are described in Pure & Appl. Chem., Vol. 67, Nos 8/9, pp. 1257-1306, 1995.

In another embodiment, the treatment unit is a catalytic dechlorination zone. The catalytic dechlorination zone comprises a catalyst that even in the absence of the ionic liquid catalyst causes some removal of the alkyl chloride in the chlorinated-hydrocarbon. In one embodiment the dechlorination conditions in the catalytic dechlorination zone include a LHSV of 0.05 to 50, a carrier gas/chlorinated-hydrocarbon molar ratio of 0.5 to 20, a total unit pressure of 10 to 1,000 psig, and a catalyst bed temperature from 65.6° C. (150° F.) to 343° C. (650° F.). In one embodiment, the catalyst bed temperature is from 93.3° C. (200° F.) to 343° C. (650° F.).

In one embodiment the ionic liquid catalyst has accumulated in the distillation unit during prior distilling of the chlorinated-hydrocarbon. The ionic liquid catalyst can accumulate in the distillation unit by allowing a trace amount of a carry-over ionic liquid catalyst to be fed to the distillation unit. In one embodiment, this accumulation of the ionic liquid catalyst can occur in the distillation unit even when the chlorinated-hydrocarbon comprises less than 10 ppmw, or less than 5 ppmw, of the ionic liquid catalyst. After the ionic liquid catalyst has accumulated in the treatment unit the ionic liquid catalyst can become active for the removal of the alkyl chloride in the chlorinated-hydrocarbon.

Chloride Removal

The treatment unit is operated such that at least 75 wt % of the chlorides are removed from the chlorinated-hydrocarbon. In one embodiment, at least 90 wt % of the chlorides are removed. In another embodiment, greater than 92 wt %, greater than 94 wt %, greater than 96 wt %, or greater than 97 wt % up to 99.9 wt % of the chlorides are removed from the chlorinated-hydrocarbon.

In one embodiment the dechlorinated hydrocarbon comprises less than 100, less than 75, less than 65, less than 50, less than 30, or less than 25 ppmw chlorides. In one embodiment, the dechlorinated hydrocarbon comprises from 1 to 25 ppmw chlorides.

The conditions for operating the treatment unit can include an elevated temperature, such as a temperature from 65.6° C. (150° F.) to 343° C. (650° F.), a temperature from 93.3° C. (200° F.) to 316° C. (600° F.), or a temperature from 121° C. (250° F.) to 288° C. (550° F.). The pressure can be any pressure that is effective for removing the chlorides. The amount of the ionic liquid catalyst in the treatment unit can be from 20 ppmw to 2 wt %, but not so high that it converts the chlorinated-hydrocarbon into undesirable by-products. When the ionic liquid catalyst is fed together with the chlorinated-hydrocarbon to the treatment unit, the amount of the ionic liquid catalyst is adjusted to an effective amount. For example, the chlorinated-hydrocarbon can be mixed with 0.001 to 0.1 wt % of the ionic liquid catalyst when feeding to the treatment unit.

Hydrogen Chloride Production

In one embodiment, the alkyl chlorides in the chlorinated-hydrocarbon are able to be removed after being converted to dechlorinated-hydrocarbon and HCl in the treatment unit due to elevated temperatures and the presence of small amounts of ionic liquid catalyst. In one embodiment, the removal of the alkyl chloride in the chlorinated-hydrocarbon is induced by catalytic cracking of the alkyl chloride and the removal produces the HCl.

In one embodiment, the HCl that is produced in the treatment unit can be recovered from the treatment unit. The recovered HCl can be recovered and used in another process. For example, the HCl can be recycled back to a hydrocarbon conversion reactor that produces a hydrocarbon product that comprises the chlorinated-hydrocarbon.

Dechlorinated-Hydrocarbon

The dechlorinated-hydrocarbon has a significantly lower level of chlorides than the chlorinated-hydrocarbon that is originally fed to the treatment unit. In one embodiment, the dechlorinated-hydrocarbon is an alkylate gasoline blending component. An alkylate gasoline blending component can be blended into gasoline or used directly as gasoline. Examples of alkylate gasoline blending components are naphtha and heavy naphtha. In the context of this disclosure, naphtha has a boiling range distribution less than 130° C. and heavy naphtha has a boiling range distribution from 130 to 200° C. In one embodiment, the alkylate gasoline blending component has a Research Octane Number (RON) from 80 to 105. In one embodiment, the alkylate gasoline blending component has a Motor Octane Number (MON) from 80 to 105.

RON is determined using ASTM D 2699-12, Standard Test Method for Research Octane Number of Spark-Ignition Engine Fuel. Additionally, the RON (GC) can be calculated from gas chromatography boiling range distribution data. The RON (GC) calculation is described in the publication, Anderson, P. C., Sharkey, J. M., and Walsh, R. P., "Journal Institute of Petroleum", 58 (560), 83 (1972).

In one embodiment, a second RON of the dechlorinated-hydrocarbon that is an alkylate gasoline blending component is within 5 points, within 3 points, within 2 points, or within 1 point of a first RON of the chlorinated-hydrocarbon. In one embodiment, the second RON is greater than the first RON.

In one embodiment, the final boiling point of the dechlorinated-hydrocarbon is not significantly different from the final boiling point of the chlorinated-hydrocarbon fed to the treatment unit, further indicating that the treated hydrocarbon product is not degraded. For example, a second final boiling point of the dechlorinated-hydrocarbon can be within 5 degrees C., within 3 degrees C., within 2 degrees C., or within 1 degree C. of a first final boiling point of the chlorinated-hydrocarbon. Final boiling point is the maximum temperature observed on a distillation thermometer when a distillation is carried out on the dechlorinated-hydrocarbon or chlorinated-hydrocarbon. The test methods used for boiling range distributions (including final boiling points) of the hydrocarbons in this disclosure are ASTM D 2887-08 and ASTM D 6352-04 (Reapproved 2009). The boiling range distribution determination by distillation is simulated by the use of gas chromatography. The boiling range distributions obtained by these test methods are essentially equivalent to those obtained by true boiling point (TBP) distillation (see ASTM Test Method D 2892), but are not equivalent to results from low efficiency distillations such as those obtained with ASTM Test Methods D 86 or D 1160.

In one embodiment, the dechlorinated-hydrocarbon has both a RON and a final boiling point that are not significantly changed by the process. For example, the second RON of the dechlorinated-hydrocarbon can be within 2 points of the first RON of the chlorinated-hydrocarbon and the second final boiling point of the dechlorinated-hydrocarbon can be within 5 degrees C. of the first final boiling point of the chlorinated-hydrocarbon.

EXAMPLES

Example 1

Ionic Liquid Catalyst Comprising Anhydrous Metal Halide

Various ionic liquid catalysts made of anhydrous metal halides such as $AlCl_3$, $AlBr_3$, $GaCl_3$, $GaBr_3$, $InCl_3$, and $InBr_3$ could be used for the catalytic processes. N-butylpyridinium chloroaluminate ($C_5H_5C_4H_9Al_2Cl_7$) ionic liquid catalyst is one example that is used in our process. The catalyst had the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Example 2

Alkylation of $C_3/C_4$ Olefin and Isobutane to Make Alkylate Gasoline

Refinery isobutane containing 85% isobutane and 15% n-butane was used for an alkylation study, after drying the refinery isobutane with 13× molecular sieve. A refinery olefin stream containing $C_3$ and $C_4$ olefins ($C_3/C_4$ Olefin) from a Fluid Catalytic Cracking Unit (FCC unit) was dried with 13× molecular sieve and isomerized with a $Pd/Al_2O_3$ catalyst at 150° F. (65.6° C.), and 250 psig in the presence of hydrogen to produce an isomerized $C_3$ and $C_4$ olefin feed with the composition shown in Table 1.

TABLE 1

Composition of Olefin Feed

| Composition | Mol % |
|---|---|
| Propane, C3 | 13.3 |
| Propylene, C3 = | 25.4 |
| 1-Butene, 1-C4 = | 2.3 |
| 2-Butene, 2-C4 = | 16.2 |
| Isobutylene, i-C4 = | 6.7 |
| n-Butane, nC4 | 12.4 |
| Isobutane, iC4 | 22.2 |
| C5+ | 1.6 |
| Sum | 100.0 |

An alkylation of the isomerized $C_3$ and $C_4$ olefin feed, described above, with the dried refinery isobutane was performed in a continuously stirred tank reactor. An 8:1 molar mixture of the isobutane and the olefin was fed to the reactor while vigorously stirring. An ionic liquid catalyst as described in Example 1 was fed to the reactor via a second inlet port, and targeted to occupy 6 vol % in the reactor. A small amount of n-butyl chloride was added to produce anhydrous HCl gas in situ. The average residence time in the reactor (combined volume of feeds and catalyst) was about 12 minutes. The outlet pressure was maintained at 200 psig and the reactor temperature was maintained at 95° F. (35° C.) using external cooling.

The reactor effluent was separated with a coalescing separator into a hydrocarbon phase and an ionic liquid catalyst phase. The coalescer was effective in separating the ionic liquid catalyst from the hydrocarbon phase. The amount of ionic liquid in the hydrocarbon phase was less than 5 ppmw. The "ionic-liquid free" hydrocarbon phase was sent to a series of distillation columns to separate the hydrocarbon phase into multiple streams. The $1^{st}$ distillation column operated at 150° F. (65.6° C.) reboiler temperature and 110 psig pressure, and separated the hydrocarbon phase into an $iC_4-$ fraction and a $nC_4+$ fraction. The $nC_4+$ fraction was send to a second distillation column operated at 101.7° C. (215° F.) reboiler temperature and 60 psig pressure to generate an n-butane product and an alkylate product. The $iC_4^-$ fraction (the overhead of the $1^{st}$ column) was sent to a $3^{rd}$ distillation column operated at 54.4° C. (130° F.) reboiler temperature and 5 psig pressure to produce a gas stream containing a $C_3-$ fraction in the overhead fraction and isobutane in the bottom fraction. The isobutane from the bottom fraction was recycled back to the alkylation reactor.

The alkylate product from the bottom of the $2^{nd}$ distillation column was analyzed by X-ray Fluorescence (XRF) Spectroscopy to determine the chloride content in ppm-weight. The alkylate samples showed 500-600 ppmw of alkyl chloride.

Example 3

Reduction of Alkyl Chloride in Alkylate by Ionic Liquid Catalyst Injection to the Distillation Column The same process conditions described in Example 2 were used in two tests, except that approximately 100 ppmw of the ionic liquid catalyst, described in Example 1, was sent to the first distillation column along with the hydrocarbon phase.

To examine the effect of the ionic liquid catalyst for alkyl chloride reduction, the hydrocarbon phases were sampled before and after distillation. The samples before distillation were taken after the coalescer overhead to the first distillation column inlet. A 0.5 µm on-line filter was used when sampling the coalescer overhead to prevent any contamination of the hydrocarbon samples with ionic liquid catalyst. The coalescer overhead samples contained a large excess of isobutane and required weathering for 12-18 hours before they were analyzed.

The hydrocarbon samples taken after distillation (i.e., dechlorinated alkylate) were taken from the bottom of the $2^{nd}$ distillation column. All of the samples were analyzed by X-ray Fluorescence (XRF) Spectroscopy to determine the chloride content in ppm-weight and by Gas Chromatography (GC) to determine if there was any degradation due to exposure of the alkylate to the ionic liquid catalyst during the distillation. The chloride results are summarized in Table 2. The compositional properties of the test samples in this example were analyzed to examine whether the alkylate quality was degraded by the small amount of the ionic liquid catalyst that had accumulated in the distillation column. The compositional analyses for the samples produced in Test #1 are shown in Table 3.

TABLE 2

Removal of Alkyl Chloride with Ionic Liquid Catalyst in Distillation Column

| | Chloride Before Distillation, ppmw | Chloride After Distillation, ppmw | Chloride Removal, % |
|---|---|---|---|
| Test #1 | 623 | 29 | 95 |
| Test #2 | 686 | 62 | 91 |

TABLE 3

Compositional Analysis of Alkylate with Ionic Liquid Catalyst in Distillation Columns

| | Before Distillation, Weathered Alkylate with 686 ppmw Cl | After Distillation, Product Alkyate with 62 ppmw Cl |
|---|---|---|
| C5+ Composition, wt % | | |
| C5 | 11.1 | 14.1 |
| C6 | 6.6 | 7.7 |
| C7 | 25.8 | 25.5 |
| C8 | 38.0 | 37.1 |
| C9 | 12.4 | 10.8 |
| C10 | 3.6 | 2.8 |
| C11+ | 2.6 | 1.9 |
| Sum | 100 | 100 |
| RON (GC) | 87.5 | 87.8 |
| MON | 87.4 | 87.5 |
| (RON + MON)/2 | 87.4 | 87.7 |

The above results, in comparison with the results in Example 2, clearly show that addition of a small amount of ionic liquid catalyst to the distillation column effectively removed alkyl chloride species from the alkylate in the distillation column and produced a dechlorinated-hydrocarbon that was high quality alkylate gasoline.

GC analyses of the two alkylate products, before and after the distillation columns, showed slight increases in the Research and Motor Octane Numbers, and the amount of trimethylpentanes was not significantly changed. These results support that the quality of alkylate was not degraded, or was slightly improved, by the addition of ionic liquid catalyst to the distillation column.

While we do not want to be bound by theory, we believe that the alkyl chlorides in the chlorinated-alkylate are being converted to olefin and HCl in the distillation columns due to elevated temperatures and the presence of small amounts of ionic liquid catalyst. This conversion of alkyl chloride in the distillation columns gave a process advantage in that the HCl produced from the conversion of the alkyl chloride in the 1$^{st}$ distillation column can be combined with HCl that is formed in the alkylation reactor in the $C_3-$ overhead gas. This combined HCl stream can then be recycled to the front end of the process as an ionic liquid catalyst promoter for alkylation.

Example 4

Reduction of Alkyl Chloride in Alkylate by Ionic Liquid Catalyst Supported on Alumina In this example, we conducted a fixed-bed-heterogeneous-catalysis with the ionic liquid catalyst from Example 1. Alkylate product was made using refinery $C_4$ mixed olefins from a FCC unit per the procedures described in Examples 2 and 3. The alkylate product was a chlorinated-hydrocarbon feed that contained 875 ppmw of alkyl chloride.

We supported the ionic liquid catalyst on alumina and compared its performance with that of an alumina support only. The supported catalyst was prepared with an in-situ impregnation method. The desired amount of alumina support (24-42 mesh) was loaded to the center of a stainless steel reactor (⅜" OD). An ionic liquid/chloroform solution with a volume equivalent to 103% of water pore volume of alumina support was fed to the reactor by a syringe pump in flowing nitrogen (3000 SCF/B). The loading of ionic liquid on the alumina support was controlled at 30 wt %. The supported catalyst was further dried at room temperature in a flow of nitrogen for one hour and then gradually heated to 300° F. (148.9 degree Celsius) at a rate of 50° F. (27.8 degree Celsius)/hour. The supported catalyst was held at 300° F. (148.9 degree Celsius) for one hour to remove the chloroform solvent.

The alkylate product was pumped to the catalytic dechlorination zone that had a fixed bed reactor containing either alumina only or the ionic liquid catalyst loaded onto alumina as described above. The dechlorination conditions in the catalytic dechlorination zone included an LHSV of 0.5 hr$^{-1}$, a carrier gas/alkylate molar ratio of 7, a total unit pressure of 100 psig, and a catalyst bed temperature of 232° C. (450° F.). Either with or without the ionic liquid catalyst on the support, the dechlorination step lowered the chloride content of the chlorinated-hydrocarbon feed to a much lower level in the dechlorinated-hydrocarbon product. Results in Table 4 below shows alkyl chloride reduction was significantly better with the ionic liquid catalyst impregnated alumina, indicating that the ionic liquid catalyst supported in a treatment unit was very effective in reducing the alkyl chloride in the alkylate.

TABLE 4

Reduction of Alkyl chloride with Ionic Liquid Impregnated Alumina Catalyst

|  | Alumina Only | Ionic Liquid Supported on Alumina |
|---|---|---|
| ppmw Cl in Alkylate Feed | 875 | 875 |
| ppmw Cl in Alkylate Product | 160 | 20 |
| % Chloride Removal | 82 | 98 |

Compositional analyses of both the alkylate feed (chlorinated-hydrocarbon feed) and the dechlorinated-hydrocarbon product made using the ionic liquid catalyst supported on alumina were performed. These compositional results are summarized in Table 5.

TABLE 5

Compositional Analysis of the Alkylates

|  | Alkylate Feed | Dechlorinated Alkylate Product, Treated with Ionic Liquid Catalyst Supported on Alumina |
|---|---|---|
| Wt % C7 | 5.7 | 5.5 |
| Wt % C8 | 61.2 | 61.9 |
| 2,2,3-trimethyl-C5, wt % | 46.1 | 46.5 |
| dimethyl-C6, wt % | 12.9 | 13.2 |
| methyl-C7, wt % | 2.1 | 2.2 |
| 2,2,3-trimethyl-C5 in C8, wt % | 75.4 | 75.2 |
| dimethyl-C6 in C8, wt % | 21.1 | 21.3 |

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:

1. A process for reducing chloride in a hydrocarbon, comprising:
   a. feeding a chlorinated-hydrocarbon, comprising greater than 50 up to 5,000 ppmw chlorides, and an ionic liquid catalyst comprising an anhydrous metal halide to a treatment unit; wherein an amount of the ionic liquid catalyst comprising the anhydrous metal halide in the treatment unit is from 20 ppmw to 2 wt %;
   b. operating the treatment unit under conditions including a temperature from 65.6° C. (150° F.) to 343° C. (650° F.), wherein the ionic liquid catalyst induces a removal of an alkyl chloride in the chlorinated-hydrocarbon to produce a dechlorinated-hydrocarbon and a HCl; and
   c. collecting the dechlorinated-hydrocarbon from the treatment unit, wherein at least 90 wt % of the chlorides have been removed from the chlorinated-hydrocarbon.

2. The process of claim 1, wherein the treatment unit comprises a distillation column.

3. The process of claim 2, wherein the ionic liquid catalyst is supported in the distillation column.

4. The process of claim 2, wherein the treatment unit comprises a series of distillation columns.

5. The process of claim 1, wherein the treatment unit is a catalytic dechlorination zone.

6. The process of claim 1, wherein the treatment unit comprises a distillation unit and the ionic liquid catalyst has accumulated in a part of the distillation unit.

7. The process of claim 6, wherein the part of the distillation unit is a distillation column, a bottom of a reboiler, a product-recycle loop, or combinations thereof.

8. The process of claim 1, wherein the chlorinated-hydrocarbon has greater than 500 ppmw chlorides.

9. The process of claim 1, wherein greater than 92 wt % up to 99.9 wt % of the chlorides have been removed from the chlorinated-hydrocarbon.

10. The process of claim 1, wherein the dechlorinated-hydrocarbon comprises less than 25 ppmw chlorides.

11. The process of claim 1, wherein the ionic liquid catalyst is fed together with the chlorinated-hydrocarbon to the treatment unit.

12. The process of claim 11, where the chlorinated-hydrocarbon is mixed with 0.001 to 0.1 wt % of the ionic liquid catalyst when feeding to the treatment unit.

13. The process of claim 1, wherein the ionic liquid catalyst is fed separately from the chlorinated-hydrocarbon to the treatment unit.

14. The process of claim 1, wherein the ionic liquid catalyst is different from a conversion-ionic liquid catalyst that was used to produce the chlorinated-hydrocarbon.

15. The process of claim 1, wherein the ionic liquid catalyst is impregnated on a porous support.

16. The process of claim 1, wherein the ionic liquid catalyst is supported on a polymer support by covalent bond interaction between the ionic liquid catalyst and the polymer support.

17. The process of claim 1, wherein the HCl is recovered from the treatment unit.

18. The process of claim 17, wherein the HCl is recycled to a hydrocarbon conversion reactor that produces the chlorinated-hydrocarbon.

19. The process of claim 17, wherein the removal of the alkyl chloride in the chlorinated-hydrocarbon is by catalytic cracking of the alkyl chloride.

20. The process of claim 1, wherein the dechlorinated-hydrocarbon is an alkylate gasoline blending component, and wherein a second RON of the dechlorinated-hydrocarbon is within 5 points of a first RON of the chlorinated-hydrocarbon.

21. The process of claim 1, wherein a second final boiling point of the dechlorinated-hydrocarbon is within 5 degrees C. of a first final boiling point of the chlorinated-hydrocarbon.

22. The process of claim 1, wherein the conditions for operating the treatment unit include the temperature from 121° C. (250° F.) to 288° C. (550° F.).

23. The process of claim 1, wherein the ionic liquid catalyst comprises an anhydrous metal halide selected from the group consisting of $AlCl_3$, $AlBr_3$, $GaCl_3$, $GaBr_3$, $InCl_3$, and mixtures thereof.

24. The process of claim 1, wherein the ionic liquid catalyst comprises a cation that is an ammonium, phosphonium, or sulphonium.

25. A process for producing a dechlorinated-hydrocarbon, comprising:
   a. creating an ionic liquid catalyst-rich zone in a distillation unit by feeding an ionic liquid catalyst comprising an anhydrous metal halide to the distillation unit;
   b. passing a chlorinated-hydrocarbon comprising a mixture of an alkylate product and an alkyl chloride to the distillation unit;
   c. operating the distillation unit under conditions including a temperature from 65.6° C. (150° F.) to 343° C. (650° F.), wherein the ionic liquid catalyst that has accumulated in the distillation unit induces a removal of the alkyl chloride to produce the dechlorinated-hydrocarbon; and wherein a second final boiling point of the dechlorinated-hydrocarbon is within 5 degrees C. of a first final boiling point of the chlorinated-hydrocarbon.

26. A process for reducing chloride in a hydrocarbon, comprising:
   a. feeding a chlorinated-hydrocarbon that is an alkylate gasoline blending component comprising greater than 50 up to 5,000 ppmw chlorides and having a first RON, and an ionic liquid catalyst comprising an anhydrous metal halide to a treatment unit;
   b. operating the treatment unit under conditions including a temperature from 65.6° C. (150° F.) to 343° C. (650° F.), wherein the ionic liquid catalyst induces a removal of an alkyl chloride in the chlorinated-hydrocarbon to produce a dechlorinated-hydrocarbon and a HCl; and
   c. collecting the dechlorinated-hydrocarbon from the treatment unit, wherein at least 90 wt % of the chlorides have been removed from the chlorinated-hydrocarbon and the dechlorinated-hydrocarbon has a second RON that is within 2 points of the first RON.

* * * * *